(12) United States Patent
Karni

(10) Patent No.: US 6,981,970 B2
(45) Date of Patent: Jan. 3, 2006

(54) DEVICE AND METHOD FOR TREATING SKIN

(75) Inventor: Ziv Karni, Kfar Shmaryahu (IL)

(73) Assignee: MSq (M²) Ltd., Caesarea (IL)

(*) Notice: Subject to any disclaimer, the term of this patent is extended or adjusted under 35 U.S.C. 154(b) by 142 days.

(21) Appl. No.: 10/319,676

(22) Filed: Dec. 16, 2002

(65) Prior Publication Data
US 2004/0116983 A1 Jun. 17, 2004

(51) Int. Cl.
*A61B 18/18* (2006.01)

(52) U.S. Cl. .............................. 606/9; 607/88; 128/898
(58) Field of Classification Search ............ 607/88–95; 606/9; 128/898
See application file for complete search history.

(56) References Cited

U.S. PATENT DOCUMENTS

| 3,638,342 A | * | 2/1972 | Winslow et al. ............... 40/406 |
| 3,818,129 A | * | 6/1974 | Yamamoto ................... 348/754 |
| 4,233,493 A |   | 11/1980 | Nath |
| 5,683,380 A |   | 11/1997 | Eckhouse et al. |
| 6,183,500 B1 | * | 2/2001 | Kohler ......................... 607/88 |
| 6,280,438 B1 | * | 8/2001 | Eckhouse et al. ............... 606/9 |
| 6,387,089 B1 |   | 5/2002 | Kreindel et al. |
| 6,626,932 B2 | * | 9/2003 | Whitehurst .................. 607/88 |
| 6,784,603 B2 | * | 8/2004 | Pelka et al. .................. 313/113 |
| 2001/0003800 A1 |   | 6/2001 | Crowley |

\* cited by examiner

*Primary Examiner*—A. Farah
(74) *Attorney, Agent, or Firm*—Mark M. Friedman

(57) ABSTRACT

A method for the cosmetic treatment of skin, especially for epilation, skin remodeling and treatment of acne whereby an appropriate cosmetically effective wavelength of light is produced using a fluorescent material pumped with ultraviolet light from an ultraviolet light source.

6 Claims, 4 Drawing Sheets

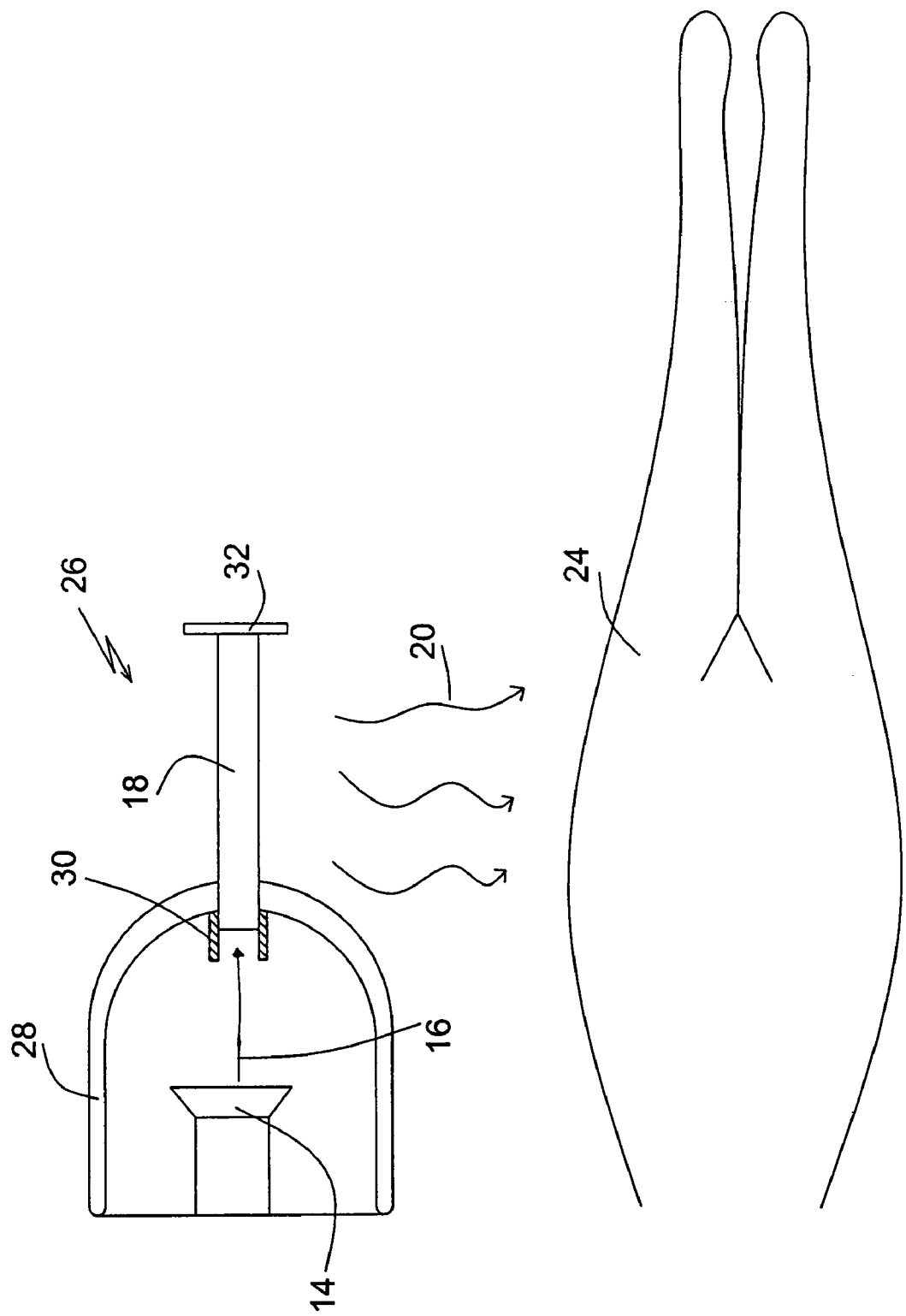

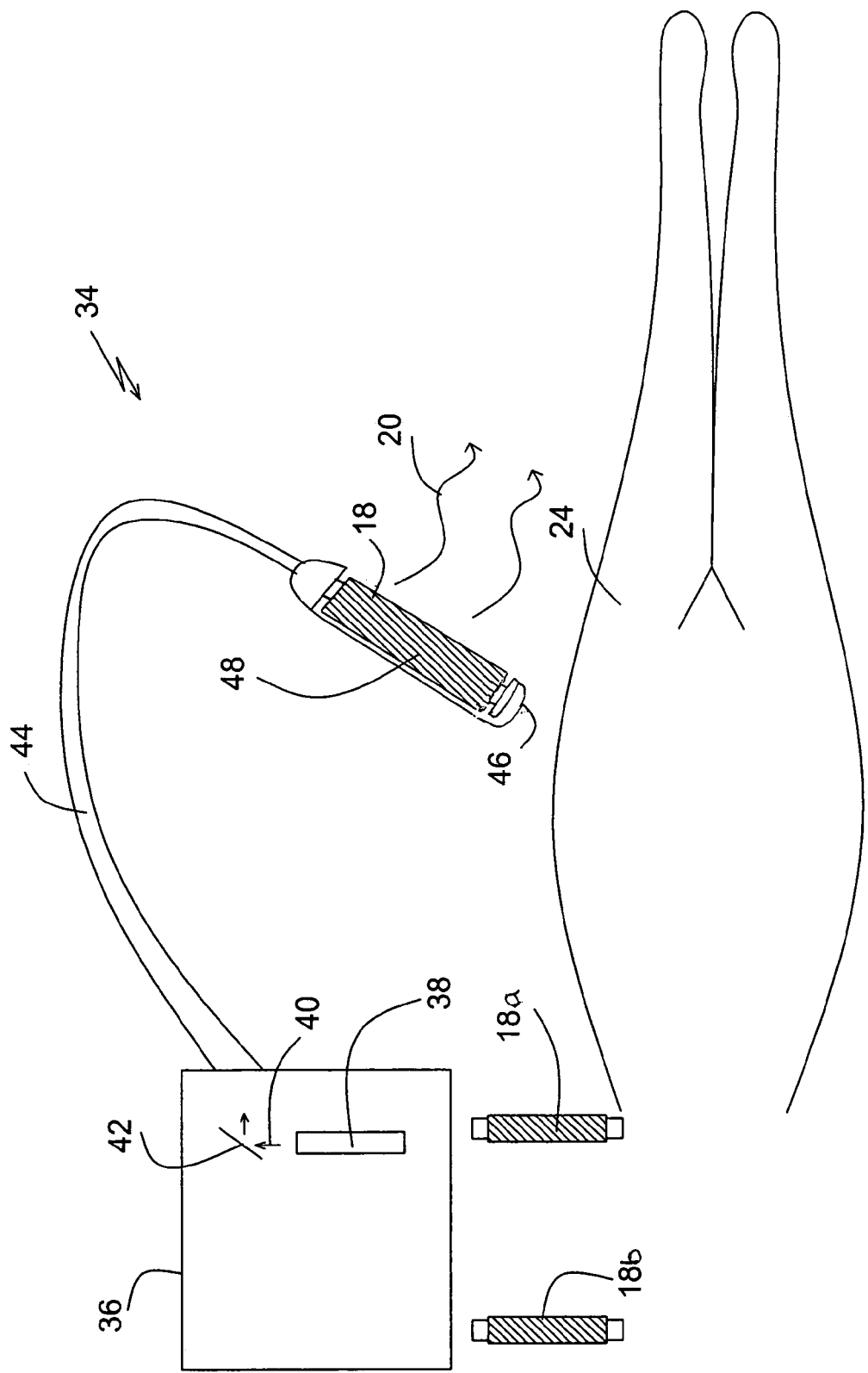

DEVICE AND METHOD FOR TREATING SKIN

FIELD AND BACKGROUND OF THE INVENTION

The present invention relates to the field of cosmetics, and more particularly to methods and a device for performing cosmetic procedures of the skin including epilation, skin rejuvenation, and the reduction of acne-related bacteria.

Supplying services in the field of cosmetic treatments is an important industry. Such services run the gamut from non-invasive procedures like hair cutting and application of lacquer to finger nails to surgical procedures developed for medically necessary reconstructive surgery.

Skin treatments are much sought after cosmetic treatments. A customer seeking a skin treatment typically desires to modify the appearance of the skin from a present state to a state that is more "youthful": smooth, elastic, homogeneously colored and textured. Hairs, creases, wrinkles, scars, shading and texture irregularities are all anathema: the removal or concealing thereof a sought after service.

In the art it is well known that the irradiation of the skin with certain specific wavelengths of light at relatively high intensities can contribute to the improvement of the appearance of the skin.

It is known in the art that irradiation with blue light can assist in alleviating the external symptoms of acne. Sebaceous gland found in the skin produce sebum. Ordinarily the sebum migrates out of the hair follicle along the hair. When a follicle is clogged, the sebum is trapped and becomes a breeding ground for bacteria, especially propionbacterium acne. The bacteria as well as the accumulating sebum lead to the appearance of an offensive looking pustule ("pimple") on the skin that may lead to permanent scarring. One method for treating acne is irradiation of an effected area with blue light having a wavelength of about 420 nm. When such light is sufficiently intense, endogenic porphyrins are produced. The porphyrins destroy propionbacterium acne, preventing the production of pimples.

It is known in the art that irradiation with red light can assist in epilation. When a hair follicle is heated to a sufficiently high temperature, the hair follicle is destroyed. Specific red wavelengths have been found to penetrate to the follicle and heat it to coagulation, yet not bum the skin itself. Details and background of the use of light for epilation can be found in U.S. Pat. Nos. 5,683,380 and 6,280,438 which are incorporated by way of reference as if fully set forth herein.

It is known in the art that irradiation with green light can be used in "skin remodeling". Green light of sufficient intensity is absorbed by subcutaneous blood vessels causing damage. The natural healing processes of the damage includes the growth of collagen fibers, giving the skin a smoother and more elastic appearance. Details and background of the use of light for skin remodeling can be found in U.S. Pat. No. 6,387,089 which is incorporated by way of reference as if fully set forth herein.

Lasers are a preferred light source in the field of cosmetic skin treatments. Lasers are energetic and monochromatic, allowing efficient treatment with little collateral damage and few side effects. However, lasers are not versatile and a single device can be used for only a specific cosmetic treatment. Further, the price of a laser based skin treatment device is prohibitively expensive Lamps, and especially flash lamps, have been used in devices useful for cosmetic skin treatments, see for example, U.S. Pat. Nos. 4,233,493, 5,683,380, 6,280,438 and 6,387,089. Flash lamps produce a broad wavelength distribution. This allows for great versatility as any cosmetic treatment can be performed: appropriate filters are placed so as to allow only the desired light to reach the skin. However the use of filters is wasteful, as only a small percentage of light energy produced by the lamp is found in any specific wavelength. The amount of energy of any one wavelength is low so that flash lamp treatments need to be repeated quite often. Further, the fear of exposing the skin to harmful ultraviolet light, abundantly produced by flash lamps, is so high that lamps and filters are chosen so as not to emit wavelengths of less than 500 nm.

In U.S. Pat. No. 6,387,089 a skin remodeling device includes a flash lamp, producing light having 500–2000 nm, fitted with filters preventing the passage of light more energetic than at least 550 nm.

In U.S. Pat. No. 6,280,438 an epilation device includes a flash lamp, producing light having 500–1300 nm or having 300 nm to 1000 nm, fitted with filters preventing the passage of ultraviolet light.

In U.S. Pat. No. 5,683,380 taught the use of a xenon flash lamp having most energy emitted as light with a wavelength of 200 nm to 1300 mm range and fitted with filters to remove lower wave lengths.

There is a need for a device that can be used for cosmetic treatments that overcomes the disadvantages of the prior art devices.

SUMMARY OF THE INVENTION

The above and other objectives are achieved by the innovative illumination device provided by the present invention.

The present invention provides for cosmetic treatment of the skin by pumping a fluorescent material with ultraviolet light and then using cosmetically useful light produced by fluorescence to perform the cosmetic treatment. Since fluorescence is both an efficient and a substantially monochromatic process, a large fraction of ultraviolet light produced by a light source is converted to cosmetically useful light.

Practice of either the device or method of the present invention is based on providing a light source having an ultraviolet component to illuminate a fluorescent material. By ultraviolet component is meant the percentage of energy radiated by the light source with a wavelength of between 200 nm and 400 nm of the total energy radiated with a wavelength of between 200 nm and 1200 nm.

According to the teachings of the present invention there is provided a cosmetic skin treatment device comprising a fluorescent material (the fluorescent material pumped by ultraviolet light and emitting cosmetically useful light) and an ultraviolet light source. By ultraviolet light source is meant a self-contained source of light having an ultraviolet component of at least 10%, whether coherent, incoherent, continuous or flashing (pulsed), preferably being a lamp or a laser. Typical such light sources include ultraviolet lasers, Xe flash lamps or Xe—Hg flash lamps.

Clearly the higher the ultraviolet component of the light source the better, at least 15% being preferred, more preferred at least 25%, even more preferred at least 40% and most preferred more than 50% ultraviolet component.

Generally, the light source of the present invention will be contained within a non-transparent housing with the fluorescent material acting as a window. The housing prevents any light from reaching the skin except where desired and directs the desired light (both from the fluorescent material and from the light source) in the desired direction. It is understood that the housing can include such features as baffles and light passages.

Clearly, harmful or otherwise undesired light may pass through the "window" made up of the fluorescent material to the skin. According to a feature of the present invention, cosmetically useful light from fluorescence is directed at the skin, but ultraviolet light produced by the light source and not absorbed by the fluorescent material is substantially prevented from reaching the skin.

According to a feature of the present invention a filter that is not transparent to ultraviolet light (for example, reflects or absorbs the ultraviolet light) is positioned in such a way so that undesired light from the light source is prevented from passing in the cosmetically useful direction (see FIG. 1, below). According to different feature of the present invention, the light source is positioned in the housing so that light from the light source does not travel in the cosmetically useful direction (see, for example, FIGS. 2 and 3).

According to a feature of the present invention, the cosmetically useful light is substantially red, substantially blue or substantially green. Herein by "substantially red" is meant a wavelength of between 620 nm and 790 nm, by "substantially blue" is meant a wavelength of between 450 nm and 495 nm and by "substantially green" is meant a wavelength of between 485 nm and 580 nm.

According to a further feature of the present invention the light source is a flash lamp and produces light flashes with a density of between 1 and 200 j cm$^{-2}$.

There is also provided according to the teachings of the present invention method for cosmetic treatment of the skin by a) providing a fluorescent material, the fluorescent material pumped by ultraviolet light and emitting cosmetically useful light, b) pumping the fluorescent material with ultraviolet light produced by a light source, and c) directing the cosmetically useful light emitted by the fluorescent material at an area of the skin to be treated cosmetically. By ultraviolet light source is meant a self-contained source of light having an ultraviolet component of at least 10%, whether coherent, incoherent, continuous or flashing (pulsed), preferably being a lamp or a laser. Typical such light sources include ultraviolet lasers, Xe flash lamps or Xe—Hg flash lamps.

According to a feature of the present invention, the area of skin is hirsute and said cosmetically useful light is substantially red. According to a further feature of the present invention, the area of skin is afflicted with acne and said cosmetically useful light is substantially blue. According to a still further feature of the present invention, the area of skin needs remodeling and said cosmetically useful light is substantially green.

BRIEF DESCRIPTION OF THE DRAWINGS

The invention is herein described, by way of example only, with reference to the accompanying drawings, wherein:

FIG. 3 is a schematic depiction of a second embodiment of an illumination device of the present invention; and FIG. 4 is a schematic depiction of a third embodiment of an illumination device of the present invention.

DESCRIPTION OF THE PREFERRED EMBODIMENTS

The present invention is of an innovative illumination device, which allows for safe and efficient irradiation of selected areas with selected wavelengths of light. Use of the device of the present invention allows performance of, amongst others, three common cosmetic procedures.

All illumination devices of the present invention are based on converting the light of commonly available ultraviolet light sources to light useful in the field of cosmetic treatments using fluorescence.

Figure 1:
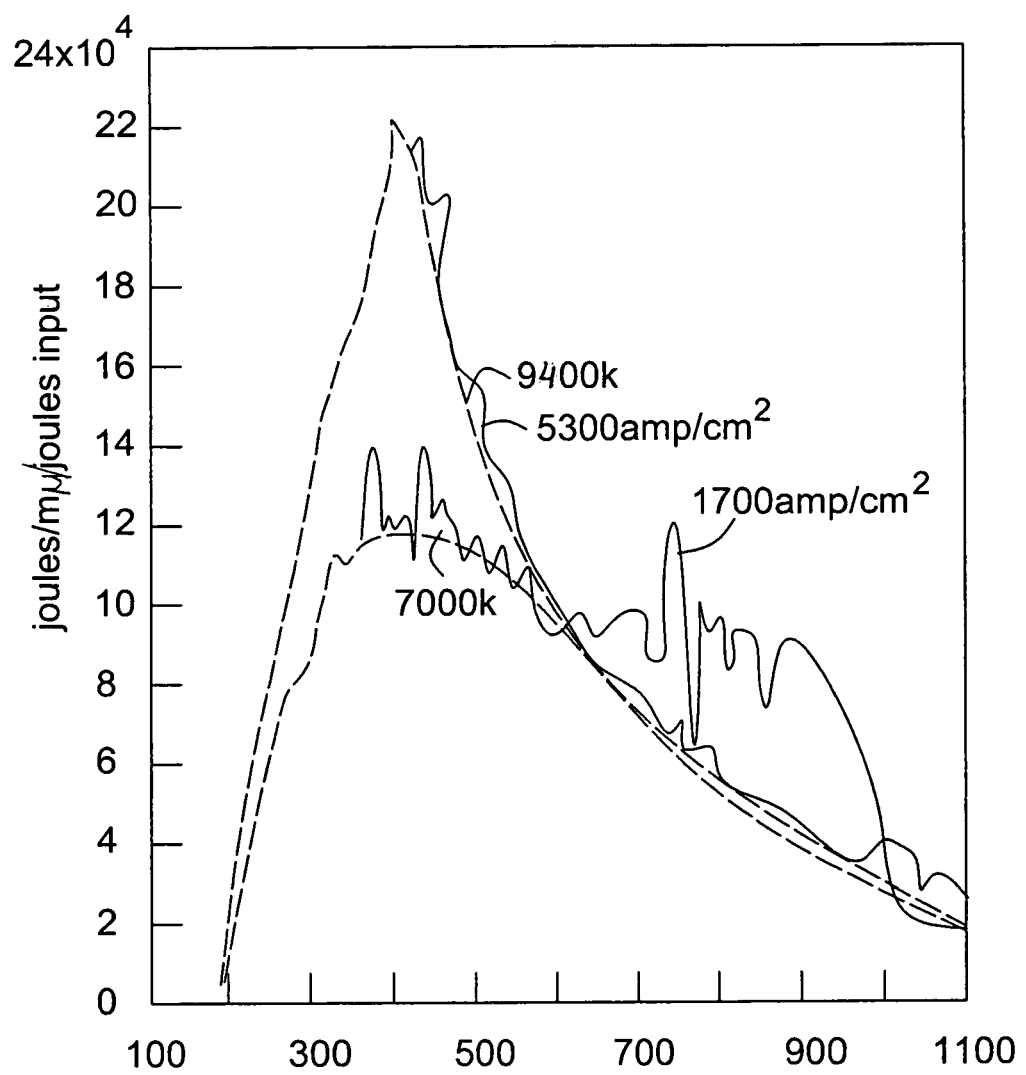
FIG. 1 is the emission spectrum of a high-pressure xenon lamp.

In FIG. 1 is depicted the emission spectrum of a Quartz-envelope high-pressure xenon lamp (such as manufactured by, for example, Perkin-Elmer Optoelectronics (Fremont, Calif., USA) or Xenon corporation (Woburn, Mass., USA)). One skilled in the art recognizes that cosmetically useful wavelengths make up only a fraction of total energy output while the lion's share of radiation is harmful ultraviolet light. Use of such a lamp to treat the skin of a person is clearly undesirable. However, when used in accordance with the present invention, the ultraviolet radiation produced by the lamp is efficiently converted to cosmetically useful light.

Figure 2:
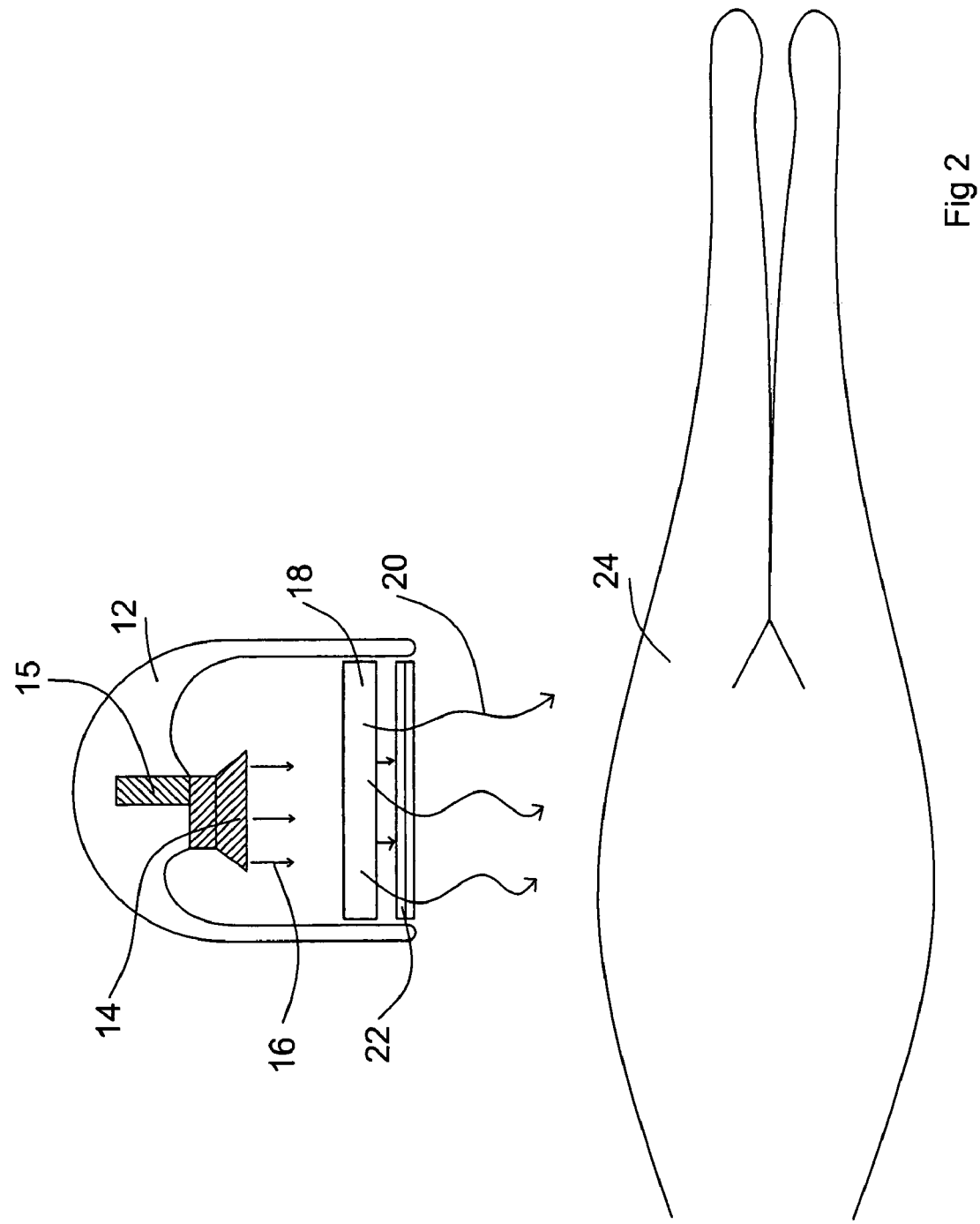
FIG. 2 is a schematic depiction of a first embodiment of an illumination device of the present invention.

A first embodiment of an illumination device of the present invention 10 is schematically depicted in FIG. 2. Inside a light proof housing 12 is found a water-cooled quartz-envelope high-pressure xenon flash lamp 14 fitted with a reflector. Further in illumination device 10 is found electrical pulse-forming network, 15 (such as manufactured by Perkin-Elmer Optoelectronics (Fremont, Calif., USA). Pulse forming network 15 allows flash lamp 14 to produce single or trains of flashes. A typical pulse-forming network can cause a xenon flash lamp, such as 14, to generate single or a train of light flashes with a total density of 1 to 200 j cm$^{-2}$ and having a flash width of between 0.5 and 200 millseconds in duration.

When activated, flash lamp 14 repetitively produces intense flashes of light 16 over a wide range of wavelengths, with a large ultraviolet component. Ultraviolet pumped fluorescent block 18 absorbs ultraviolet light and re-emits light of a desired wavelength 20. Filter 22 prevents harmful or otherwise undesirable light 16 produced by flash lamp 14 from exiting the confines of device 10 in the direction of skin 24. As a result, from device 10 only safe (that is non-ultraviolet) light exits to illuminate skin 24 for treatment. Further, due to the presence of ultraviolet pumped fluorescent block 18, the intensity of light of the desired wavelength 20 produced is much higher than prior art non-laser cosmetic illumination devices.

A second embodiment of an illumination device of the present invention 26 is schematically depicted in FIG. 3. Inside a light proof housing 28 is found a high-pressure xenon lamp 15. When activated, lamp 15 produces intense light 16 over a wide range of wavelengths, with a large ultraviolet component. Ultraviolet pumped fluorescent block 18 absorbs ultraviolet light and re-emits light of a desired wavelength 20. Baffles 30 which make up part of light proof housing 28 are positioned so that all light produced by lamp 15 and not confined to light proof housing 28 passes through ultraviolet pumped fluorescent block 18 in the direction of non-transparent block 32. Light produced by lamp 15 is therefore either used to pump fluorescent block 18 or harmlessly confined within device 26. In such a way skin 24 is illuminated only with light of desired wavelength 20 produced by ultraviolet pumped fluorescent block 18.

A third embodiment of an illumination device 34 of the present invention is schematically depicted in FIG. 4. Inside casing 36 is found a laser 38 that efficiently produces ultraviolet light 40 (such as produced by Thermo Laser Science of Mountain View, Calif., USA). A first mirror 42 directs ultraviolet light 40 into a glass fiber light guide (Sumita Optical Glass, Inc. Saitama-Urawa, Japan) 44. Glass fiber light guide 44 directs ultraviolet light 40 to a second mirror 46. Second mirror 46 directs ultraviolet light 40 back through glass fiber light guide 44. In the path of ultraviolet light 38 is interposed ultraviolet pumped fluorescent block 18, held in place by fluorescent block holder 48. Ultraviolet light 40 produced by laser 38 is used to pump fluorescent block 18 or is harmlessly confined within casing 36 and glass fiber light guide 44. In such a way skin 24 is illuminated only with light of desired wavelength 20 produced by ultraviolet pumped fluorescent block 18. It is important to note that casing 36, glass fiber light guide 44, and second mirror 46 are all components making up the housing of device 34.

All three devices, 10, 26 and 34, can be configured for a specific treatment by simply changing the nature of ultraviolet pumped fluorescent block 18. It is a simple matter to supply a device having a plurality of ultraviolet pumped fluorescent blocks such as 18 that are configured so as to be easily replaceable. In FIG. 3, ultraviolet pumped fluorescent block 18 is depicted as being replaceable, with fluorescent blocks 18a and 18b. Fashioning appropriately shaped, fitted and designed fluorescent blocks 18, 18a and 18b and block holder 46 is well within the abilities of one skilled in the art after study of the description herein. Other variations and possibilities of allowing the replacement and changing of the fluorescent material in a device of the present invention can be designed by one skilled in the art after study of the description herein.

One skilled in the art will recognize that illumination device 10 and illumination device 26 are most suited for the irradiation and treatment of large and non-specific skin areas. In contrast, the flexible glass fiber light guide 44 of illumination device 34 allows light to be directed more accurately to specific skin areas. The choice of which device is preferable depends on operator preference and the treatment desired. Since all three devices emit substantially no dangerous wavelengths of light, and since device 26 and device 34 emit substantially monochromatic light, little if any harm is caused by imperfect light direction or over exposure to radiation.

In order to perform epilation according to the method of the present invention, an ultraviolet pumped fluorescent material that emits substantially red light is pumped using a light source rich in ultraviolet light. Such material is manufactured and sold under the name Lumilass-R7 by Sumita Optical Glass, Inc. (Saitama-Urawa, Japan), emitting light of substantially 610 nm when pumped by light having frequencies of between 250 nm to 420 nm. Lumilass-R7 can emit with a brightness of $10^3$ lux, sufficient for cosmetic purposes.

In order to perform skin remodeling according to the method of the present invention, an ultraviolet pumped fluorescent material that emits substantially green light is pumped using a light source rich in ultraviolet light. Such material is manufactured and sold under the name Lumilass-G9 by Sumita Optical Glass, Inc. (Saitama-Urawa, Japan), emitting light of substantially 540 nm when pumped by light having frequencies between 200 nm and 390 nm. Lumilass-G9 can emit with a brightness of $10^4$ lux, sufficient for cosmetic purposes.

In order to treat acne according to the method of the present invention, an ultraviolet pumped fluorescent material that emits substantially blue light is pumped using a light source rich in ultraviolet light. Such material is manufactured and sold under the name Lumilass-B by Sumita Optical Glass, Inc. (Saitama-Urawa, Japan), emitting light of substantially 410 nm when pumped by light having frequencies between 200 nm to 400 nm. Lumilass-B can emit with a brightness of $10^3$ lux, sufficient for cosmetic purposes.

The present invention is not limited to the embodiments described herein but also relates to all kinds of modifications thereof, insofar as they are within the scope of the claims.

What is claimed is:

1. A method for cosmetic treatment of the skin comprising:
   a. providing a fluorescent material, said fluorescent material pumped by ultraviolet light and emitting cosmetically useful light primarily of a single color;
   b. pumping said fluorescent material with ultraviolet light produced by a light source producing light having at least an about 10% ultraviolet component; and
   c. directing said cosmetically useful light emitted by said fluorescent material at an area of the skin to be treated cosmetically.

2. The method of claim 1 wherein said light source is selected from a group of light sources consisting of coherent light sources, incoherent light sources, continuous lamps, flash lamps and lasers.

3. The method of claim 1 wherein said light source is lamp selected from a group of lamps consisting of Xe flash lamps and Xe—Hg flash lamps.

4. The method of claim 1 wherein said area of skin is hirsute and said single color is red.

5. The method of claim 1 wherein said area of skin is afflicted with acne and said single color is blue.

6. The method of claim 1 wherein said area of skin needs remodeling and said single color is green.

* * * * *